United States Patent
Sawchuk et al.

(10) Patent No.: US 9,592,196 B2
(45) Date of Patent: *Mar. 14, 2017

(54) METHODS AND COMPOSITIONS FOR APPLYING PHARMACOLOGIC AGENTS TO THE EAR

(71) Applicant: Regents of the University of Minnesota, Minneapolis, MN (US)

(72) Inventors: Ronald J. Sawchuk, Prior Lake, MN (US); Belinda W. Y. Cheung, New Brighton, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 56 days.

This patent is subject to a terminal disclaimer.

(21) Appl. No.: 14/283,756

(22) Filed: May 21, 2014

(65) Prior Publication Data

US 2014/0364383 A1    Dec. 11, 2014

Related U.S. Application Data

(63) Continuation of application No. 11/614,266, filed on Dec. 21, 2006, now Pat. No. 8,734,836, which is a continuation of application No. 10/306,517, filed on Nov. 27, 2002, now Pat. No. 7,220,431.

(51) Int. Cl.
| | |
|---|---|
| A61K 9/06 | (2006.01) |
| A61K 9/00 | (2006.01) |
| A61K 31/43 | (2006.01) |
| A61K 31/545 | (2006.01) |
| A61K 31/546 | (2006.01) |
| A61K 31/7048 | (2006.01) |
| A61K 31/716 | (2006.01) |
| A61K 31/4402 | (2006.01) |
| A61K 31/5386 | (2006.01) |
| A61K 31/5415 | (2006.01) |
| A61K 47/34 | (2006.01) |

(52) U.S. Cl.
CPC ............ *A61K 9/0046* (2013.01); *A61K 31/43* (2013.01); *A61K 31/4402* (2013.01); *A61K 31/5386* (2013.01); *A61K 31/545* (2013.01); *A61K 31/546* (2013.01); *A61K 31/5415* (2013.01); *A61K 31/7048* (2013.01); *A61K 31/716* (2013.01); *A61K 47/34* (2013.01)

(58) Field of Classification Search
CPC .. A61K 9/0012; A61K 9/0014; A61K 9/0046; A61K 9/06
USPC ........................................ 424/437, 484–488
See application file for complete search history.

(56) References Cited

U.S. PATENT DOCUMENTS

| | | |
|---|---|---|
| 4,034,759 A | 7/1977 | Haerr |
| 4,188,373 A | 2/1980 | Krezanoski |
| 4,478,822 A | 10/1984 | Haslam |
| 5,057,502 A | 10/1991 | Walsh |
| 5,290,552 A | 3/1994 | Sierra et al. |
| 5,350,580 A | 9/1994 | Muchow et al. |
| 5,421,818 A | 6/1995 | Arenberg |
| 5,512,055 A | 4/1996 | Domb et al. |
| 5,674,196 A | 10/1997 | Donaldson et al. |
| 6,027,744 A | 2/2000 | Vacanti et al. |
| 6,043,225 A | 3/2000 | Shor et al. |
| 6,093,417 A | 7/2000 | Petrus |
| 6,149,944 A | 11/2000 | Jeong et al. |
| 6,201,072 B1 | 3/2001 | Rathi et al. |
| 6,245,347 B1 | 6/2001 | Zhang et al. |
| 6,261,547 B1 | 7/2001 | Bawa et al. |
| 6,284,804 B1 * | 9/2001 | Singh et al. ............... 514/772.4 |
| 6,319,513 B1 | 11/2001 | Dobrozsi |
| 6,365,635 B1 | 4/2002 | Nomura et al. |
| 6,440,964 B1 | 8/2002 | Cagle et al. |
| 6,723,714 B2 | 4/2004 | Hanna |
| 7,220,431 B2 | 5/2007 | Sawchuk et al. |
| 7,888,370 B2 | 2/2011 | Singh et al. |
| 8,734,836 B2 * | 5/2014 | Sawchuk et al. ............. 424/437 |
| 2001/0049366 A1 | 12/2001 | Singh et al. |
| 2002/0022629 A1 | 2/2002 | Cagle et al. |
| 2002/0052404 A1 * | 5/2002 | Hunter ................. A61K 9/0024 |
| | | 514/449 |

(Continued)

FOREIGN PATENT DOCUMENTS

| | | |
|---|---|---|
| CN | 1650863 | 8/2005 |
| CN | 101072571 | 11/2007 |
| DE | 1138890 | 10/1962 |
| EP | 694310 A | 1/1996 |
| EP | 0733357 | 9/1996 |
| EP | 1312366 | 10/2007 |
| JP | 2002-525317 A | 8/2002 |
| JP | 2006-509791 A | 3/2006 |
| JP | 2008-523060 A | 7/2008 |

(Continued)

OTHER PUBLICATIONS

Arrieta et al, "Moxifloxacin vs amoxicillin/clavulanate in the treatment of acute sinusitis," *Am J. Otolaryngol.*, 28(2):78-82, Mar.-Apr. 2007.

(Continued)

*Primary Examiner* — Micah-Paul Young
(74) *Attorney, Agent, or Firm* — Fish & Richardson P.C.

(57) ABSTRACT

Methods and materials useful for applying pharmacologic agents to the ear are described. The methods involve delivering a composition that contains at least one viscogenic agent and at least one pharmacologic agent to the epidermal surface of the tympanic membrane via the ear canal. The composition is delivered to the tympanic membrane in a flowable form and, after delivery to the tympanic membrane, becomes sufficiently viscous such that the pharmacologic agent is localized against the tympanic membrane. Such compositions can be used to prophylactically and/or therapeutically treat middle and inner ear conditions, including otitis media.

22 Claims, 2 Drawing Sheets

(56) References Cited

U.S. PATENT DOCUMENTS

| | | |
|---|---|---|
| 2003/0139382 A1 | 7/2003 | Wall et al. |
| 2004/0204471 A1* | 10/2004 | Seibert ............ A61K 31/00 514/406 |
| 2004/0204671 A1* | 10/2004 | Stubbs et al. .......... 604/26 |
| 2007/0098679 A1 | 5/2007 | Sawchuk et al. |
| 2007/0212343 A1 | 9/2007 | Owen |
| 2009/0209574 A1 | 8/2009 | Owen et al. |
| 2009/0270345 A1 | 10/2009 | Ketelson et al. |
| 2009/0306128 A1 | 12/2009 | Campins et al. |
| 2012/0289541 A1 | 11/2012 | Sawchuk et al. |

FOREIGN PATENT DOCUMENTS

| | | |
|---|---|---|
| WO | WO 00/018386 | 4/2000 |
| WO | WO 01/22936 | 4/2001 |
| WO | WO 2004/050021 A2 | 6/2004 |
| WO | WO 2006/065301 A2 | 6/2006 |
| WO | WO 2009/142719 | 11/2009 |

OTHER PUBLICATIONS

Cárceles et al., "Pharmacokinetics of moxifloxacin in rabbits after intravenous, subcutaneous and a long-acting poloxamer 407 gel formulation administration," *J Vet Med A Physiol Pathol Clin Med.*, 53(6):300-304, Aug. 2006.

Charles Ross & Son Company, "Ross inline slim makes consistently high quality carbopol solutions for cosmetic applications," *Application Data*, COS-ME-006, retrieved from the internet at www.rossmixing.com on Sep. 9, 2005, 3 pages.

Huang et al., "Microdialysis studies of the middle ear distribution kinetics of amoxicillin in the awake chinchilla," *J. Pharm. Sci.*, 2001, 90(12):2088-2098.

Jossart et al., "An experimental model for measuring middle ear antimicrobial drug penetration in otitis media," *Pharm. Res.*, 1990, 7(12):1242-1247.

Mitterando, "Ask the Doctor: Earwax not a sign of bad hygiene," *The Patriot Ledger*, retrieved from.The internet at www.healthcaresouth.com/pages/askthedoctor/earwax.htm on Sep. 9, 2005.

Ogbru, "Amoxicillin" Medicinenet, retrieved from the internet Sep. 9, 2005 at www.midicinenet.com/amoxicillin/article.htm, copyright 1996-2005, 3 pages.

Owens and Ambrose, Chapter 7: Pharmacodynamics of Quinolones, *Antimicrobial Pharmacodynamics in Theory and Clinical Practice*, 2001, p. 162, 24 pages.

Schentag et al., "Infectious Diseases: Fluoroquinolone Auic break points and the link to bacterial killing rates. Part 1: In vitro and animal models," *Ann. Pharmacother.*, 2003, 37(9):1287-1298.

Schentag et al., "Infectious Diseases: Fluoroquinolone AUIC break points and the link to bacterial . killing rates. Part 2: human trials," *Ann. Pharmacother.*, 2003, 37(10):1478-1488.

Schmolka, "Poloxamers in the Pharmaceutical Industry," *Polymers for Controlled Drug Delivery*, Chapter 10, Tharcha (ed.), CRC Press, Inc., Boca Raton, Florida, 1991, pp. 189-214.

Veyries et al. "Controlled release of vancomycin from Poloxamer 407 gels," *International Journal of Pharmaceutics* 192(2):183-193 (1999)

Wong et al., "Stability of cefazolin in Pluronic F-127 Gels," *Drug Devel. and Indus. Pharm.* 23(6):603-605 (1997)

Supplementary European Search Report in EP 03 79 6467, mailed Nov. 30, 2009,2 pages.

International Search Report for PCT/US2003/037819, mailed Jun. 21, 2004, 1 page.

Coles et al., "A comparative study of clarithromycin and amoxycillin suspensions in the treatment of pediatric patients with acute otitis media," Infection., 21(4):272-278, Jul.-Aug. 1993.

Devi et al., "Poloxamer: A novel functional molecule for drug delivery and gene therapy," J. Pharm. Sci. Res., 5(8):159-165, 2013.

McCarty et al., "Comparative safety and efficacy of clarithromycin versus amoxicillin/clavulanate in the treatment of acute otitis media in pediatric patients," Current therapeutic research., 55(9):1016-1026, Sep. 30, 1994.

Wikipedia, "Poloxamere," Retrieved from the Internet: <URL: https://de.wikipedia.org/wiki/Poloxamere>, 2 pages, Aug. 2014.

Observations by a third party in European Application No. 03796467.3 communication dated Feb. 8, 2016, 35 pages.

* cited by examiner

METHODS AND COMPOSITIONS FOR APPLYING PHARMACOLOGIC AGENTS TO THE EAR

CROSS-REFERENCE TO RELATED APPLICATIONS

This application is a continuation of and claims the benefit of priority under 35 U.S.C. §120 to U.S. application Ser. No. 11/614,266 having a filing date of Dec. 21, 2006, which is a continuation of and claims the benefit of priority under 35 U.S.C. §120 to U.S. application Ser. No. 10/306,517 having a filing date of Nov. 27, 2002. The disclosure of the prior application is incorporated by reference in its entirety.

TECHNICAL FIELD

The invention relates to methods and materials for applying pharmacologic agents to the ear. More particularly, the invention features methods and materials for applying pharmacologic agents to the external, epidermal surface of a tympanic membrane for treating disorders of the ear.

BACKGROUND

Otitis media (OM) is very common, especially in children. OM often begins with a viral infection of the upper respiratory tract that alters the micro-environment of the upper respiratory tract, Eustachian tube, and middle ear such that bacteria resident in the nasopharynx invade and populate the middle ear. This invasion can inflame and block the Eustachian tube, interfering with middle ear ventilation, pressure equilibration, and drainage. Fluids accumulate and pressure increases in the normally air-filled middle ear space, causing great pain. In severe cases of OM, sound perception structures can be damaged. Persistent or recurrent OM may be caused by bacteria that emerge from dormancy in the middle ear, having been shielded from antibiotics by a slimy biofilm.

OM currently is treated using antibiotics and/or by inserting a tympanostomy tube through a surgical incision in the tympanic membrane so as to drain and depressurize the middle ear space. The efficacy of antibiotic treatment is limited by the route of delivery. Antibiotics can be delivered systemically, but a high dose often is required to attain therapeutic levels (i.e., above minimum inhibitory concentration) in the middle ear, and such levels often are attained after a significant lag time. Antibiotics also can be delivered by lavage, or via drops into the ear canal. Such delivery routes can be difficult to control, and often are not effective to achieve prolonged therapeutic levels of antibiotic in the middle ear. Antibiotics also can be delivered by injection into the middle ear, or by inserting antibiotic-impregnated materials into the middle ear, but such methods involve piercing or cutting the tympanic membrane, which requires general anesthesia and can damage the tympanic membrane. Surgical insertion of tympanostomy tubes also carries risks, including tympanoclerosis (i.e., scarring of the tympanic membrane), hearing loss, persistent otorrhea (i.e., discharge of pus from the tube) and infection.

The National Institute on Deafness and Other Communication Disorders (NIDCD), a part of the National Institutes of Health, recently launched a $2,000,000 funding initiative to support the development of alternative strategies and new approaches for preventing and treating OM. In its request for applications (RFA-DC-02-002), NIDCD stated that: (1) OM causes significant childhood morbidity and is increasingly affecting general public health; (2) OM is the leading reason for Emergency Room visits; (3) OM is the second leading reason for doctors' office visits; (4) OM is the leading reason of childhood antibiotics prescriptions, accounting for more than 40% of all outpatient antibiotic prescriptions; (5) OM is the leading reason for childhood hearing loss; and (6) OM is the leading reason for general anesthesia in children. In addition, NIDCD blamed the use of broad-spectrum antibiotics to treat OM for the alarming emergence of multiple antibiotic resistant bacteria in three of the genera that can cause OM (*Streptococcus pneumoniae*, non-typeable *Haemophilus influenzae*, and *Moraxella catarrhalis*). As a consequence, many first and second line antibiotics are becoming less and less effective against OM and other diseases, including pneumonia and meningitis. NIDCD concluded that "the development of novel approaches for the study, treatment and prevention of OM is urgently needed to: 1) reduce OM morbidity and the associated costs; and 2) preserve the efficacy of antibiotics used for the treatment of OM and other common serious diseases."

SUMMARY

The invention is based, in part, on the discovery that compositions containing one or more pharmacologic agents can be formulated such that that they can be delivered to the external, epidermal surface of the tympanic membrane in a liquid-like form, then, upon delivery, transform to a solid-like state such that the composition remains localized against the tympanic membrane. Delivery of such compositions to the tympanic membrane can provide more effective ways to treat middle and inner ear disorders (e.g., OM).

In one aspect, the invention features a method for administering a pharmacologic agent to a mammal (e.g., a rodent or a human). The method includes applying a formulation to the epidermal surface of a tympanic membrane of the mammal, wherein the formulation includes a viscogenic agent and at least one pharmacologic agent, wherein the formulation has a viscosity less than 100,000 cps, and wherein the formulation, after application to the tympanic membrane, has a yield stress sufficient to maintain the formulation against the tympanic membrane. The viscogenic agent can be gellan, N-isopropyl acrylamide with sodium acrylate and n-N-alkylacrylamide, polyacrylic acid with polyethylene glycol, polymethacrylic acid with polyethylene glycol, CARBOPOL® (polyacrylic acid) with hydroxypropylmethylcellulose, cellulose acetate hydrogen phthalate latex, sodium alginate, or a reverse thermosetting gel such as a poloxamer or a poloxamine. The pharmacologic agent can be an antibiotic, an anti-fungal, or an anti-viral agent. The pharmacologic agent can transfer across the tympanic membrane into the middle ear space. The antibiotic can be a penicillin, e.g., amoxicillin or amoxicillin-clavulanate. The antibiotic can be a sulfa-based combination, e.g., erythromycin-sulfisoxazole or trimethoprim-sulfamethoxazole. The antibiotic can be a macrolide/azide, e.g., azithromycin or clarithromycin. The antibiotic can be a cephalosporin, e.g., cefaclor, cefprozil, cefuroxime axetil, loracarbef, cefdinir, cefixime, cefpodoxime proxetil, ceftibuten, or ceftriaxone. The at least one pharmacologic agent can include an antibiotic and an anti-inflammatory agent, and further can include an anesthetic. The formulation further can include an adhesion facilitator, a permeability enhancer, a bioadhesive, a hygroscopic agent, an ear war softener, or a preservative.

In another aspect, the invention features a kit that includes a formulation and instructions indicating that the formulation is to be applied to a tympanic membrane, wherein the formulation includes a viscogenic agent and at least one pharmacologic agent, wherein the formulation has a viscosity less than 100,000 cps, and wherein the formulation has a yield stress sufficient, after application to the tympanic membrane, to maintain the formulation against the tympanic membrane.

The invention also features a rodent (e.g., a chinchilla) that includes a formulation applied to the epidermal surface of its tympanic membrane, wherein the formulation includes a viscogenic agent and at least one pharmacologic agent, wherein the formulation has a viscosity less than 100,000 cps, and wherein the formulation has a yield stress sufficient to be maintained against the tympanic membrane.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
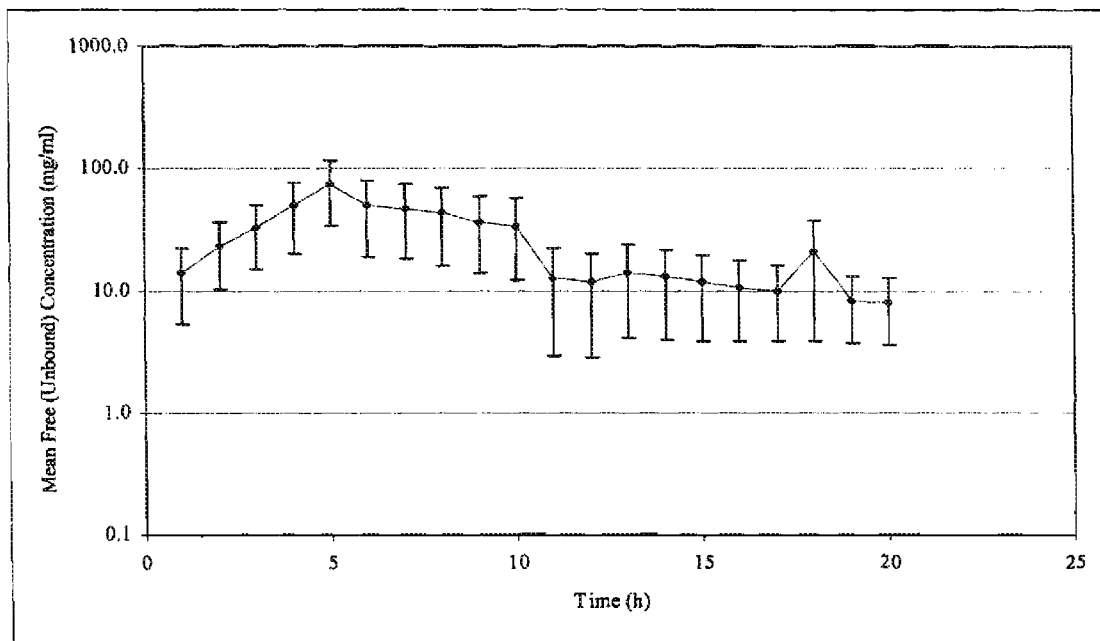
FIG. 1 is a graph of free (unbound) amoxicillin concentration in chinchilla middle ear fluid as a function of time after drug dosing via the external ear canal; mean data and standard error bars (n=3 to 5 at each time point).

In general, the invention provides methods for applying pharmacologic agents to the ear using compositions containing one or more pharmacologic agents and one or more viscogenic agents. Compositions are specifically formulated such that they can be delivered to the external, epidermal surface of the tympanic membrane in a liquid-like state, i.e., a flowable form. After administration, however, the composition transforms into a solid-like state such that the composition remains in contact with the tympanic membrane. As a result, the composition remains localized against the tympanic membrane and the pharmacologic agent can transfer across the tympanic membrane into, for example, the middle ear space, providing a more effective way to treat middle and inner ear disorders (e.g., OM). Suitable compositions also can contain other constituents, e.g., to facilitate the adhesion of the formulation to the tympanic membrane and/or to increase the permeability of the tympanic membrane to a pharmacologic agent.

Compositions of the invention have a viscosity of less than 100,000 centipoise (cps) at 25° C. Viscosity refers to the composition's resistance to flow. Compositions having a volume of 0.5 mL that can pass through a 19-gauge needle attached to a 1-mL tuberculin syringe in less than 1 minute at 25° C., by reasonable force and without aid of mechanical devices, typically have a viscosity of less than 100,000 cps.

Viscosity of a composition can be determined using a viscometer (e.g., from Brookfield) calibrated with commercially available viscosity standards.

Compositions of the invention also have a minimum yield stress that is sufficient for maintaining the formulation against the tympanic membrane. Yield stress refers to the amount of force that, when applied to a solid material, causes the solid material to exhibit liquid-like behavior in that it continues to deform with no further increase in stress. Minimum yield stress of compositions of the invention is dependent on the thickness of the applied gel, but is independent of the geometry of the gel and the temperature of the environment. As used herein, minimum yield stress of the composition is in reference to an applied gel that has a thickness of 4 mm and a density of 1 g/L. Yield stress ($\sigma_0$) is represented as $\sigma_0 = \rho g h$, where $\rho$ is the density, g is the acceleration due to gravity, and h is the layer thickness. Typically, minimum yield stress is about 39 pascals (Pa). Methods described herein also can be used to estimate if a composition has sufficient yield stress to be maintained against the tympanic membrane. For example, a test composition can be administered to the ear of an animal such as a chinchilla and the ear of the animal can be monitored to determine if the composition transforms to a more solid-like state and is maintained against the tympanic membrane. See Example 1.

Viscogenic Agents

As used herein, viscogenic agent refers to a polymer or other chemical moiety that increases the viscosity of a fluid. Suitable viscogenic agents, when included in a composition of the invention, allow the composition to transform from a liquid-like state (e.g., flowable) at 25° C. to a solid-like state (e.g., a gel) after contact with the tympanic membrane, and can be non-biodegradable, i.e., not broken down by chemicals or enzymes naturally present in a mammal, or biodegradable. Compositions include an amount of viscogenic agent effective to yield a viscosity of the composition of less than 100,000 cps at 25° C. (e.g., less than 90,000, 60,000, 30,000, 20,000, or 10,000 cps) and, generally, a minimum yield stress of 39 Pa after application to the tympanic membrane. Typically, a composition includes 0.05 to 50% of a viscogenic agent (e.g., 0.15 to 25, 5 to 45, 10 to 40, 12 to 37, 15 to 35, 17 to 33, or 20 to 30% of a viscogenic agent).

Exemplary viscogenic agents include gellan (GELRITE® or KELCOGEN®), CARBOPOL® 940 (polyacrylic acid) with hydroxypropylmethylcellulose (HPMC), N-isopropyl acrylamide (NiPAAm) with sodium acrylate and n-N-alkylacrylamide, polyacrylic acid with polyethylene glycol (PEG) or polymethacrylic acid with PEG, cellulose acetate hydrogen phthalate latex (CAP), sodium alginate, and nonionic surfactants such as poloxamers (PLURONIC®) and polyoxamine (TETRONIC®) reversible temperature-dependent gelling systems. Gellan is a natural polymer, anionic deacetylated exocellular polysaccharide, secreted by *Pseudomonas elodea*. The tetrasaccharide repeating unit consists of one α-L-rhamnose, one β-D-glucuronic acid, and two β-D-glucose moieties. The in situ gelling mechanism of gellan is cation-induced (e.g., presence of calcium ions) and temperature-dependent (e.g., physiologic temperature). Gelation is thermally reversible. CARBOPOL® 940 with HPMC gels in situ in a pH-dependent manner. CARBOPOL® is the gelling agent and the HPMC is used to enhance the viscosity of the gel. NiPAAm with sodium acrylate and n-N-alkylacrylamide is a terpolymer hydrogel that can undergo a temperature based reversible sol-gel transformation. Sodium acrylate and n-N-alkylacrylamide are used to modify the properties of the hydrogel, and in particular, the transition temperature. Polyacrylic acid with PEG or polymethacrylic acid with PEG is thought to gel based on hydrogen bonding. Polyacrylic acid can be dissolved in hydroalcoholic solution and after being injected, the alcohol diffuses out causing the polymers to precipitate and gelling of the solution. CAP is a nanoparticulate system that gels in a pH-dependent manner. The active compound (pharmacologic agent) is adsorbed partially onto the surface of the polymer particles. Sodium alginate gels in the presence of calcium or other polyvalent ion.

Nonionic Surfactants such as poloxamers and poloxamines are particularly useful. Poloxamers are well known in the pharmaceutical arts and are described, for example, by Irving R. Schmolka in *Poloxamers in the Pharmaceutical Industry*, in Polymers for Controlled Drug Delivery, Chapter 10 (Peter J. Tarcha ed., 1990). Poloxamers are triblock copolymers because they are composed of two different polymer blocks (i.e., hydrophilic poly(oxyethylene) blocks and hydrophobic poly(oxypropylene) blocks) configured as a triblock of poly(oxyethylene)-poly(oxypropylene)-poly(oxyethylene). Poloxamers are one class of block copolymer surfactants having a propylene oxide block hydrophobe and an ethylene oxide hydrophile. Poloxamers are commercially available (e.g., PLURONIC® polyols are available from BASF Corporation). Alternatively, polaxamers can be synthesized by known techniques.

Poloxamers previously have been thought to lack utility for administering pharmacologic agents, given their non-biodegradability, their water solubility and their relatively rapid drug release kinetics (see e.g., U.S. Pat. No. 6,201,072). Nonetheless, as described herein, poloxamers share a property that is advantageous for applying formulations to the tympanic membrane: aqueous formulations of poloxamers exhibit reverse thermal gelation, or reverse thermosetting. When an aqueous poloxamer formulation is heated over its gelation temperature, its viscosity increases and it transforms into a gel. When an aqueous poloxamer formulation is cooled below its gelation temperature, its viscosity decreases and it transforms into a liquid. The transition between gel and liquid does not involve a change in the chemical composition of the formulation, and is reversible and repeatable. The gel-liquid transition temperature of an aqueous poloxamer formulation can be adjusted by one of ordinary skill in the art using routine experimentation (e.g., by manipulating poloxamer concentration, pH and presence of other ingredients in the formulation). In some embodiments, compositions have a gelation temperature that is greater than the ambient temperature and less than or equal to the temperature of the tympanic membrane. Such compositions can be conveniently applied via an individual's ear canal as a liquid and then can transform into a gel against the tympanic membrane, thereby maintaining the drug in the formulation in close proximity to the tympanic membrane.

Pharmacologic Agents

A composition of the invention also contains at least one pharmacologic agent (i.e., a chemical or biological molecule that has a desired effect when applied in an effective amount to the tympanic membrane). The amount of pharmacologic agent present in the composition is dependent on the type of pharmacologic agent and its known effective dosage. Typically, pharmacological agents are present in amounts ranging from 0.1% to 50% (e.g., 0.25% to 15%). A composition can include any type of pharmacologic agent, including, e.g., an adrenocorticoid (corticosteroid, steroid), analgesic, analgesic adjunct, analgesic-anesthetic, anesthetic, antibiotic, antibacterial, anti-infective, antibiotic therapy adjunct, antidote, anti-emetic, anti-fungal, anti-inflammatory, anti-vertigo, anti-viral, biological response modifier, cytotoxic, diagnostic aid, immunizing agent, immunomodulator, proteins, peptides, and other agents that may useful in treating ear disorders. Analgesic, analgesic adjunct, analgesic-anesthetic, anesthetic, antibiotic, antibacterial, anti-infective, antibiotic therapy adjunct, anti-fungal, anti-inflammatory, anti-viral, and peptides are particularly useful. A composition of the invention can include a plurality of pharmacologic agents, including two or more agents within the same class (e.g., two different antibiotics) or two or more agents of various types, depending on the effect desired. For example, to fight a bacterial infection, to reduce tissue inflammation, and to alleviate irritation, a composition can contain an antibacterial, an anti-inflammatory, and an anesthetic or analgesic. Those skilled in the art can identify pharmacologic agents and combine them as needed to achieve a desired effect.

Exemplary adrenocorticoids include betamethasone, cortisone, dexamethasone, hydrocortisone, methylprednisolone, paramethasone, prednisolone, prednisone, and triamcinolone. Exemplary analgesics include acetaminophen, aspirin, buprenorphine, butalbital, butorphanol, codeine, dezocine, diflunisal, dihydrocodeine, etodolac, fenoprefen, fentanyl, floctafenine, hydrocodone, hydromorphone, ibuprofen, ketoprofen, ketorolac, levorphanol, magnesium salicylate, meclofenamate, mefenamic acid, meperidine, meprobamate, methadone, methotrimeprazine, morphine, nalbuphine, naproxen, opium, oxycodone, oxymorphone, pentazocine, phenobarbital, propoxyphene, salsalate, and sodium salicylate. One exemplary analgesic adjunct is caffeine. Exemplary anesthetics include articane-epinephrine, bupivacaine, chloroprocaine, etidocaine, ketamine, lidocaine, mepivacaine, methohexital, prilocalne, propofol, propoxycaine, tetracaine, and thiopental. One exemplary analgesic-anesthetic is antipyrine-benzocaine.

Exemplary antibiotics, anti-bacterials, and anti-infectives include sulfonamides (e.g., sulfanilamide, sulfadiazine, sulfamethoxazole, sulfisoxazole, para-aminobenzoic acid, or sulfacetamide), trimethoprim-sulfamethoxazole, quinolones (e.g., ciprofloxacin, ofloxacin, or nalidixic acid), β-lactam antibiotics such as penicillins or cephalosporins, aminoglycosides (e.g., kanamycin, tobromycin, gentamycin C, amikacin, neomycin, netilmicin, streptomycin, or vancomycin), tetracyclines, chloramphenicol, and macrolides (e.g., erythromycin, clarithromycin, or azithromycin). Non-limiting examples of suitable penicillins include penicillin G, penicillin V, methicillin, oxacillin, nafeillin, ampicillin, and amoxicillin. Non-limiting examples of suitable cephalosporins include cephalothin, cefdinir, cefozolin, cephalexin, cefadraxal, cefamandole, cefoxitin, cefaclor, cefonicid, cefoletan, cefotaxime, ceftizoxime, cefrtriaxone, cefditoren, and cefepine. Exemplary antibiotics useful for treating OM include penicillins such as amoxicillin and amoxicillin-clavulanate (AUGMENTIN®); sulfa-based combinations such as erythromycin-sulfisoxazole (Pediazole), trimethoprim-sulfamethoxazole (BACTRIM®, SEPTRA®); macrolides/azalides such as azithromycin (ZITHROMAX®) or clarithromycin (BIAXIM®); second-generation cephalosporins such as cefaclor (CECLOR®), cefprozil (CEFZIL®), cefuroxime axetil (CEFTIN®), or loracarbef (LORABID®); and third generation cephalosporins such as cefdinir (OMNICEF®), cefixime (SUPRAX®), cefpodoxime proxetil (VANTIN®), ceftibuten (CEDAX®), cefditoren (SPECTRACEF™), and ceftriaxone (ROCEPHIN®).

Suitable anti-emetics include buclizine, chlorpromazine, cyclizine, dimenhydrinate, diphenhydramine, diphenidol, domperidone, dronabinol, haloperidol, hydroxyzine, meclizine, metoclopramine, nabilone, ondansetron, perphenazine, prochlorperazine, promethazine, scopolamine, thiethylperazine, triflupromazine, and trimethobenzamine. Exemplary antifungals include amphotericin B, clioquinol, clotrimazole, fluconazole, flucytosine, griseofulvin, ketoconazole, miconazole, and potassium iodide. Exemplary anti-inflammatory agents include aluminum acetate, aspirin, betamethasone, bufexamac, celecoxib, dexamethasone, diclofenac, etodolac, flurbiprofen, hydrocortisone, indomethacin, magnesium salicylate, naproxen, prednisolone, rofecoxib, salsalate, sulindac, and triamcinolone. Exemplary anti-vertigo agents suitable for the invention include belladonna, dimenhydrinate, diphenhydramine, diphenidol, meclizine, promethazine, and scopolamine. Exemplary antiviral agents suitable for the invention include acyclovir, amantadine, delavirdine, didanosine, efavirenz, foscarnet, ganciclovir, indinavir, nelfinavir, ribavirin, ritonavir, zalcitabine, and zidovudine. Exemplary biological response modifiers include aldesleukin, interferon α-2a, interferon α-2b, interferon α-n1, interferon α-n3, interferon γ, and levamisole. Exemplary cytotoxic agents include podofilox and podophyllum. Exemplary immunizing agents include influenza virus vaccine, pneumococcal vaccine polyvalent, and immune globulin. An exemplary immunomodulator invention is interferon γ. Other pharmacologic agents suitable for the invention include betahistine (e.g., for treating the nausea, dizziness, and ringing in the ears that occur in Ménière's disease), prochlorperazine, and hyoscine.

Other Constituents of Compositions of the Invention

In some embodiments, compositions of the invention include one or more compounds in addition to the viscogenic and pharmacologic agents. For example, a composition can include one or more of the following compounds: a solvent or diluent such as saline, a bioadhesive, a permeability enhancer, a hygroscopic agent, an earwax softener, preservative (e.g., an antioxidant), or other additives. Such compounds can be present in the composition in amounts ranging from 0.01% to 99% (e.g., 0.01 to 1, 0.01 to 10, 0.01 to 40, 0.01 to 60, 0.01 to 80, 0.5 to 10, 0.5 to 40, 0.5 to 60, 0.5 to 80, 1 to 10, 1 to 40, 1 to 60, 1 to 80, 5 to 10, 5 to 40, 5 to 60, 5 to 80, 10 to 20, 10 to 40, 10 to 60, 10 to 80, 20 to 30, 30 to 40, 40 to 50, 50 to 60, 60 to 70, or 70 to 80%). For example, a composition can include one or more viscogenic agents (e.g., PLURONIC® F-127 and CARBOPOL®), one or more pharmacologic agents, and one or more permeability enhancers (e.g., vitamin E). In other embodiments, a composition can include one or more viscogenic agents, one or more pharmacologic agents, and one or more earwax softeners. Compositions also can include one or more viscogenic agents, one or more pharmacologic agents, one or more hygroscopic agents, and one or more preservatives. It is noted that certain agents can fulfill different roles within the formulation. For example, CARBOPOL® can function as a viscogenic agent or as a bioadhesive, depending on its concentration. Vitamin E can function as a permeability enhancer, a preservative, and an antioxidant.

A bioadhesive facilitates the adhesion of the composition to the tympanic membrane. Suitable bioadhesives include hydrocolloids such as: acacia; agar agar; alginates (e.g., alginic acid and sodium alginate); CABOPOL®; carboxymethylcellulose sodium; carboxymethylcellulose calcium; dextran; gelatin; guar gum; heparin; hyaluronic acid; hydroxyethylcellulose; karaya gum; methylcellulose; pectin; polyacrylic acid; polyethylene glycol; poly-N-vinyl-2-pyrrolidone; and tragacanth.

Permeability enhancers increase the permeability of the tympanic membrane to a pharmacologic agent. Exemplary permeability enhancers include: alcohols (e.g., ethanol and isopropanol); polyols (e.g., n-alkanols, limonene, terpenes, dioxolane, propylene glycol, ethylene glycol, and glycerol); sulfoxides (e.g., dimethylsulfoxide, dimethylformamide, methyl dodecyl sulfoxide, and dimethylacetamide); esters (e.g., isopropyl myristate/palmitate, ethyl acetate, butyl acetate, methyl proprionate, and capric/caprylic triglycerides); ketones; amides (e.g., acetamides); oleates (e.g., triolein); surfactants (e.g., sodium lauryl sulfate); alkanoic acids (e.g., caprylic acid); lactams (e.g., azone); alkanols (e.g., oleyl alcohol); dialkylamino acetates; polyunsaturated fatty acids (e.g., linoleic, alpha-linolenic, and arachidonic); oleic acid; cod-liver-oil; menthol derivatives (e.g., l-menthol); Squalene; glycerol monoethers derived from linear saturated fatty alcohols; flavones (e.g., chamomile apigenin, luteolin, and apigenin 7-O-β-glucoside); vitamin E (α-tocopherol) and esters and analogs thereof; and Senkyu (Ligustici Chuanxiong Rhizome) ether extract.

Hygroscopic agents such as fructose, phthalic acid, and sorbitol, facilitate the transfer of fluid from the middle ear across the tympanic membrane into the gel matrix. Hygroscopic agents can help alleviate pain associated with fluid accumulation and pressurization of the middle ear, and can concentrate a pharmacologic agent in smaller fluid volume in the middle ear.

Earwax softeners (e.g., docusate, olive oil, sodium bicarbonate, urea, or hydrogen peroxide) facilitate contact between the tympanic membrane and the composition. An antioxidant such as ascorbic acid and benzoic acid or other preservatives can be used to extend the shelf life of the formulation during storage.

Methods of Applying a Composition to the Tympanic Membrane

A composition of the invention can be applied to the epidermal surface of a tympanic membrane via the external auditory canal to, for example, treat a middle or inner ear disorder (e.g., OM). Compositions of the invention also can be applied prophylactically (e.g., to prevent the development of a middle or inner ear disorder). A composition can be targeted to any part of the tympanic membrane, including the pars tensa, the lower part of the tympanic membrane, or pars flaccida, the upper part of the tympanic membrane. In adult humans, the tympanic membrane is about nine to ten mm in diameter and has a thickness ranging from 30 to 230 μm (about 100 μm on average). The pars flaccida makes up less than 3% of the tympanic membrane area in humans and animals such as cats, guinea pigs, and chinchillas. In other mammals (e.g., gerbils, rabbits, rats, and mice), the pars flaccida makes up 10% to 25% of the tympanic membrane area. A thin epidermal layer (approximately 15 to 30 μm thick) covers the human tympanic membrane, while a thick epidermal layer (approximately 75 to 150 μm thick) covers other areas of the human body. Five to ten layers of cells cover the pars flaccida, while three to five layers of cells cover the pars tensa. Thus, the pars tensa often is thinner than other parts of the tympanic membrane and may be more permeable to a pharmacologic agent. The central portion of the pars tensa provides the active vibrating area in response to sound.

Any method known in the art can be used to apply a composition of the invention to the tympanic membrane. For example, a composition can be applied to the tympanic membrane using a fluid dispensing device. A dispensing device typically has a reservoir coupled to a conducting tube that directly or indirectly receives a flowable composition from the reservoir and conducts the composition to a dispensation outlet. One of ordinary skill can make a simple dispensing device as a matter of routine from a syringe connected to flexible tubing. A dispensing device also can be made by replacing the needle of a tympanocentesis device such as the CDT® Speculum (Walls Precision Instruments LLC, Casper, Wyo., USA) with a fluid conducting tube. A dispensing device can be attached to a pneumatic or diagnostic otoscope head (e.g., from Welch Allyn®, Skaneateles Falls, N.Y., USA) to create a precise platform for applying a composition to the tympanic membrane.

Depending on the composition and the middle or inner ear disorder, it may be desirable to remove the composition from the ear. This can be accomplished manually using a cotton swab or forceps. A syringe or bulb also can be used to inject water, saline or other biocompatible aqueous solutions to soften, dissolve and/or flush out the formulation. In other embodiments, compositions simply may slough off the tympanic membrane after a period of time and fall out of the ear (e.g., during exercise or bathing). Biodegradable formulations may not need to be removed from the ear.

each formulation. Each formulation was dispensed using a 1-ml tuberculin syringe fixed to a blunted needle. With the animal's head tilted on one side and using an otoscope, the syringe was inserted into the ear canal approaching the tympanic membrane and the formulation (300 to 350 µl) was slowly dispensed. The chinchilla was maintained recumbent for about one minute, or until the formulation turned opaque, indicating that the formulation had gelled.

Blank phosphate buffer solution (PBS) was instilled into the middle ear of the chinchilla. Amoxicillin concentration in the middle ear fluid was determined by direct microdialysis sampling of the lower bullae and HPLC-UV analysis for 20 hours while the chinchilla was awake. Mean unbound (pharmacologically active) amoxicillin levels (n=3 to 5 at each time point, mean and standard error) in the middle ear fluid increased to approximately 75 µg/ml after 5 hours. See FIG. 1.

TABLE 1

| Pluronic F-127 | Solvent | ETOH (v/v) | PEG 4000 (w/v) | Tween20 (w/v) | Tween80 (w/v) | IPM (v/v) | CARBOPOL ® | Transition Temp (° C.) | Drug(s) | Final Transition Temp (° C.) |
|---|---|---|---|---|---|---|---|---|---|---|
| 20% | PBS | — | — | — | — | — | | | 0.2%* | |
| 20% | PBS | — | — | — | — | — | | | 0.02%* | |
| 20% | PBS | — | — | — | — | — | | | 0.1%* | |
| 20% | Saline | 2% | 2% | — | — | — | | | 1.5%* | |
| 20% | Saline | 2% | 2% | — | — | 3.0% | | | 1.5%* | |
| 20% | PBS | 3% | | | | | 0.20% | | 0.25%*** | |

*drug is amoxicillin;
***drug is clarithromycin

Articles of Manufacture

Compositions described herein can be combined with packaging material and sold as articles of manufacture or kits. Components and methods for producing articles of manufactures are well known. The articles of manufacture may combine one or more compositions described herein. In addition, the articles of manufacture may further include one or more of the following: sterile water or saline, pharmaceutical carriers, buffers, or fluid-dispensing devices. A label or instructions describing how the composition can be delivered to the ear for treatment of inner or middle ear disorders may be included in such kits. The compositions may be provided in a pre-packaged form in quantities sufficient for single or multiple administrations.

The invention will be further described in the following examples, which do not limit the scope of the invention described in the claims.

EXAMPLES

Example 1

Trans-Tympanic Membrane Delivery of Amoxicillin

Flowable formulations containing 20% PLURONIC® PF-127 (Sigma product number P-2443, Lot number 99H1194) and a targeted drug load ranging from 0.3 mg to 5.2 mg of amoxicillin (Sigma product number A-8523, Lot number 29F0730) were prepared for administration to the tympanic membrane of adult chinchillas via the outer ear canal. See Table 1 (first five rows) for the composition of

Example 2

Trans-Tympanic Membrane Delivery of Clarithromycin

Flowable formulations containing 20% PLURONIC® PF-127 (Sigma product number P-2443, Lot number 99H1194) and 0.25% (w/v) clarithromycin (USP standard 13437, Lot number F-2) (see last row of Table 1) were administered to the tympanic membranes of adult chinchillas. The formulations had a solution to gel transition temperature of about 28° C. The formulations were administered via the outer ear canal using a 1-ml tuberculin syringe attached to a rounded oral gavage tube. With the animal's head tilted on one side and using an otoscope, the syringe was inserted into the ear canal approaching the tympanic membrane and the formulation (0.2 to 0.5 mL; clarithromycin dosage=0.5 to 1.25 mg per ear) was slowly dispensed. The chinchilla was maintained recumbent for about ten minutes to allow the formulation to gel. The solutions generally transitioned to a gel state sufficient to maintain the formulation against the tympanic membrane transition within one to two minutes after administration, as determined by otoscopy.

Figure 2:
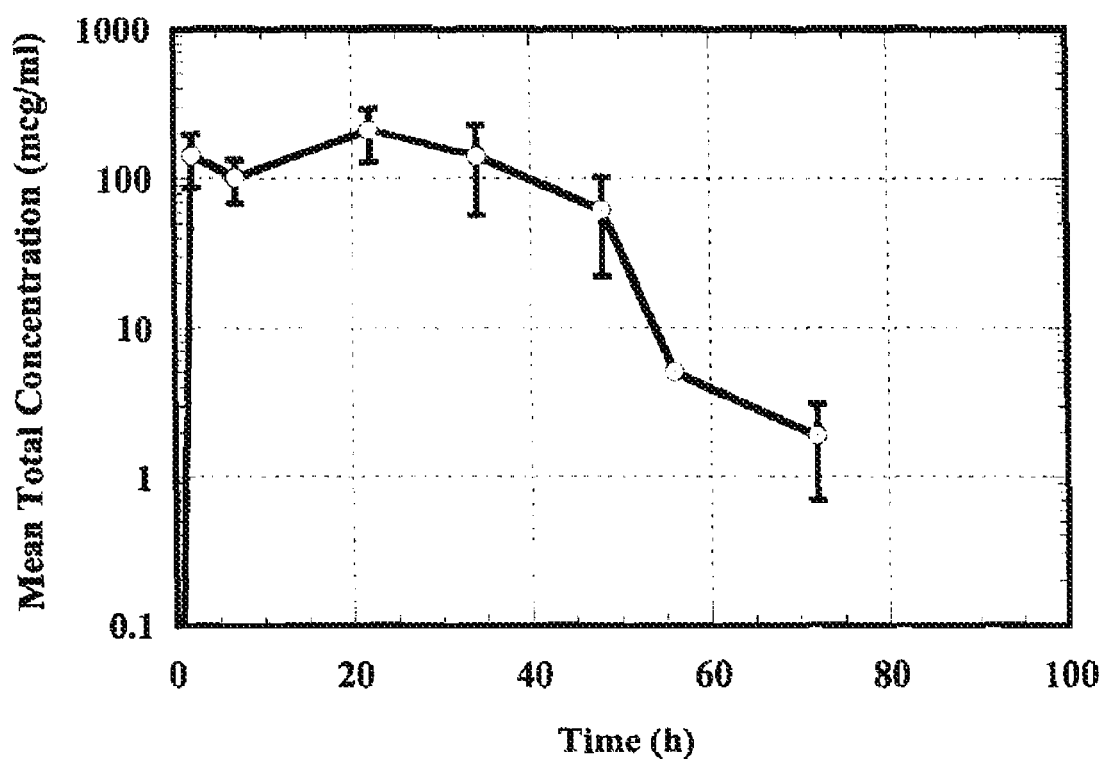
FIG. 2 is a graph of clarithromycin concentration in chinchilla middle ear fluid as a function of time after drug dosing via the external ear canal; mean data and standard error bars (n=12 to 23 at each time point).

Blank phosphate buffer solution (PBS) was instilled into the middle ear of the chinchilla. Clarithromycin concentration in the middle ear fluid was determined by direct sampling from bullae and LC-MS-MS analysis. See FIG. 2, which plots clarithromycin concentration as a function of time post-administration for 12-23 dosed ears.

Example 3

Viscosity and Yield Stress

The viscosity of the commercially available poloxamer 407 20% gel (GALLIPOT® Polox Gel 20%, preserved and buffered pH 5.0) was measured at 13.5° C. Since the transition temperature of this product is about 14.5° C., viscosity could not be measured at 25° C. The viscosity at 13.5° C. was about 350-400 cps.

Yield stress of the same product was measured at temperatures ranging from 23 to 27.5° C. after it had gelled. The measured yield stress ranged from 80 to 400 Pa, significantly higher than the minimum yield stress of 39.2 Pa required to maintain the composition against the tympanic membrane.

Example 4

Flowable Formulations

Flowable formulations containing 20% PLURONIC® PF-127 (Sigma product number P-2443, Lot number 99H1194) and one or more pharmacologic agents (e.g., 0.5 to 1.5% (w/v)) can be prepared containing the components described in Table 2.

TABLE 2

| Pluronic F-127 | Solvent | ETOH (v/v) | PEG 4000 (w/v) | Tween20 (w/v) | Tween80 (w/v) | IPM (v/v) | Transition Temp (° C.) | Final Transition Temp (° C.) |
|---|---|---|---|---|---|---|---|---|
| 20% | PBS | 3% | — | 5.0% | — | — | | |
| 20% | PBS | 3% | 2% | — | — | — | 28 | |
| 20% | PBS | 3% | — | 5.0% | — | — | 28 | <33.7 |
| 20% | PBS | 3% | — | — | 4.6% | — | 28 | 31 |
| 20% | PBS | 3% | 2% | — | — | 5.0% | 27 | <31 |
| 20% | PBS | 3% | — | — | 4.8% | — | | |
| 20% | PBS | — | — | — | 0.6% | — | | |
| 20% | PBS | — | 2% | — | — | 5.0% | | |
| 20% | PBS | — | 2% | — | — | — | | |
| 20% | PBS | — | 2% | — | — | 1.0% | | |
| 20% | PBS | — | 2% | — | — | 2.5% | | |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An aqueous composition comprising:
    A suitable amount of a viscogenic agent such that the composition has a gelation temperature is greater than the ambient temperature and less than or equal to the temperature of the tympanic membrane, wherein the composition is a liquid below the gelation temperature and is a gel over the gelation temperature, and wherein the composition comprises 5% to 45% of the viscogenic agent; a therapeutic amount of at least one pharmacologic agent; and a diluent; wherein the formulation is flowable and has a viscosity less than 100,000 cps at 25° C.

2. The composition of claim 1, wherein the viscogenic agent is selected from the group consisting of gellan, CARBOPOL 940 with hydroxypropylmethylcellulose (HPMC), N-ispropyl acrylamide (NiPAAm) with sodium acrylate and n-N-alkylacrylamide, polyacrylic acid with polyethylene glycol (PEG), polymethacrylic acid with PEG, cellulose acetate hydrogen phthalate latex (CAP), sodium alginate, poloxamers and polyoxamines.

3. The composition of claim 1, wherein the pharmacologic agent is selected from the group consisting of an adrenocorticoid, an analgesic, an analgesic adjunct, an analgesic-anesthetic, an anesthetic, an antibiotic, an antibacterial, an anti-infective, an antibiotic therapy adjunct, an antidote, an anti-emetic, an anti-fungal, an anti-inflammatory, an anti-vertigo, an anti-viral, a biological response modifier, a cytotoxic compound, a diagnostic aid, an immunizing agent, and an immunomodulator.

4. The composition of claim 3, wherein the antibiotics, anti-bacterials, and anti-infectives are selected from the group consisting of sulfonamides, trimethoprim-sulfamethoxazole, quinolones, beta-lactam antibiotics, aminoglycosides, tetracyclines, chloramphenicol and macrolides.

5. The composition of claim 1, wherein the pharmacologic agent is selected from the group consisting of betahistine, prochlorperazine, and hyoscine.

6. The composition of claim 1, wherein the diluent is saline.

7. The composition of claim 1, further comprising a bioadhesive, a permeability enhancer, a hygroscopic agent, an earwax softener, an antioxidant, or a preservative.

8. A method for delivering a pharmacologic agent to the middle ear of an individual, comprising:
    applying the composition of claim 1 to a tympanic membrane of the individual via the external ear canal.

9. An aqueous composition comprising: means for imparting, to the composition, a gelation temperature of the tympanic membrane, wherein the composition is a liquid below the gelation temperature and is a gel over the gelation temperature, and wherein the means for imparting to the composition comprise 5% to 45% of a viscogenic agent; a therapeutic amount of a least one pharmacologic agent; and a diluent; wherein the formulation is flowable and has a viscosity less than 100,000 cps at 25° C.

10. The composition of claim 9, wherein the means for imparting, to the composition, the gelation temperature that is greater than the ambient temperature and less than or equal to the temperature of the tympanic membrane is selected from the group consisting of gellan, CARBOPOL 940 with hydroxypropylmethylcellulose (HPMC), N-ispropyl acrylamide (NiPAAm) with sodium acrylate and n-N-alkylacrylamide, polyacrylic acid with polyethylene glycol (PEG), polymethacrylic acid with PEG, cellulose acetate hydrogen phthalate latex (CAP), sodium alginate, poloxamers and polyoxamines.

11. The composition of claim 9, wherein the pharmacologic agent is selected from the group consisting of an adrenocorticoid, an analgesic, an analgesic adjunct, an analgesic-anesthetic, an anesthetic, an antibiotic, an antibacterial, an anti-infective, an antibiotic therapy adjunct, an antidote, an anti-emetic, an anti-fungal, an anti-inflammatory, an anti-vertigo, an anti-viral, a biological response modifier, a cytotoxic compound, a diagnostic aid, an immunizing agent, and an immunomodulator.

12. The composition of claim 11, wherein the antibiotics, anti-bacterials, and anti-infectives are selected from the group consisting of sulfonamides, trimethoprim-sulfamethoxazole, quinolones, beta-lactam antibiotics, aminoglycosides, tetracyclines, chloramphenicol and macrolides.

13. The composition of claim 9, wherein the pharmacologic agent is selected from the group consisting of betahistine, prochlorperazine, and hyoscine.

14. The composition of claim 9, wherein the diluent is saline.

15. The composition of claim 9, further comprising a bioadhesive, a permeability enhancer, a hygroscopic agent, an earwax softener, an antioxidant, or a preservative.

16. A method for delivering a pharmacologic agent to the middle ear of an individual, comprising:
applying the composition of claim 9 to a tympanic membrane of the individual via the external ear canal.

17. The composition of claim 1, wherein the composition comprises 10% to 40% of the viscogenic agent.

18. The composition of claim 1, wherein the composition comprises 12% to 37% of the viscogenic agent.

19. The composition of claim 1, wherein the composition comprises 15% to 35% of the viscogenic agent.

20. The composition of claim 9, wherein the composition comprises 10% to 40% of the viscogenic agent.

21. The composition of claim 9, wherein the composition comprises 12% to 37% of the viscogenic agent.

22. The composition of claim 9, wherein the composition comprises 15% to 35% of the viscogenic agent.

* * * * *

UNITED STATES PATENT AND TRADEMARK OFFICE
CERTIFICATE OF CORRECTION

PATENT NO. : 9,592,196 B2
APPLICATION NO. : 14/283756
DATED : March 14, 2017
INVENTOR(S) : Ronald J. Sawchuk and Belinda W. Y. Cheung Page 1 of 1

It is certified that error appears in the above-identified patent and that said Letters Patent is hereby corrected as shown below:

In the Claims

Column 11, Line 49: In Claim 1, delete "A" and insert -- a --, therefor.

Column 11, Line 50: In Claim 1, after "temperature" insert -- that --.

Column 11, Line 63: In Claim 2, delete "N-ispropyl" and insert -- N-isopropyl --, therefor.

Column 12, Line 45: In Claim 9, after "temperature" insert -- that is greater than the ambient temperature and less than or equal to the temperature --.

Column 12, Line 49: In Claim 9, delete "comprise" and insert -- comprises --, therefor.

Column 12, Line 50: In Claim 9, delete "a least" and insert -- at least --, therefor.

Column 12, Line 58-59: In Claim 10, delete "N-ispropyl" and insert -- N-isopropyl --, therefor.

Signed and Sealed this
Thirtieth Day of January, 2018

Joseph Matal
*Performing the Functions and Duties of the*
*Under Secretary of Commerce for Intellectual Property and*
*Director of the United States Patent and Trademark Office*